(12) United States Patent
Marchini et al.

(10) Patent No.: US 10,227,609 B2
(45) Date of Patent: Mar. 12, 2019

(54) MODIFIED PARVOVIRUS USEFUL FOR GENE SILENCING

(71) Applicant: DEUTSCHES KREBSFORSCHUNGSZENTRUM, Heidelberg (DE)

(72) Inventors: Antonio Marchini, Heidelberg (DE); Jean Rommelaere, Heidelberg (DE); Barbara Leuchs, Heidelberg (DE); Anna Illarionova, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 0 days.

(21) Appl. No.: 14/355,691

(22) PCT Filed: Jan. 25, 2013

(86) PCT No.: PCT/EP2013/000224
§ 371 (c)(1),
(2) Date: May 1, 2014

(87) PCT Pub. No.: WO2013/110464
PCT Pub. Date: Aug. 1, 2013

(65) Prior Publication Data
US 2014/0310829 A1   Oct. 16, 2014

(30) Foreign Application Priority Data
Jan. 27, 2012 (EP) .................... 12000554

(51) Int. Cl.
*C12N 15/113* (2010.01)
*C12N 15/86* (2006.01)
*C12N 15/11* (2006.01)
*A01K 67/027* (2006.01)

(52) U.S. Cl.
CPC .......... *C12N 15/86* (2013.01); *A01K 67/0275* (2013.01); *C12N 15/111* (2013.01); *C12N 15/113* (2013.01); *C12N 2310/14* (2013.01); *C12N 2310/531* (2013.01); *C12N 2320/32* (2013.01); *C12N 2330/51* (2013.01); *C12N 2750/14343* (2013.01)

(58) Field of Classification Search
CPC combination set(s) only.
See application file for complete search history.

(56) References Cited

FOREIGN PATENT DOCUMENTS

WO   WO2011/116974   *   9/2011

OTHER PUBLICATIONS

Czauderna, et al. (2003) "Inducible shRNA expression for application in a prostate cancer mouse model." Nucleic Acids Research, v.31(21):e127.*
Raykov, et al. (2008) "Arming parvoviruses with CpG motifs to improve their oncosuppressive capacity." Int. J. Cancer, v.122:2880-4.*
Rommelaere, et al. (2010) "Oncolytic parvoviruses as cancer therapeutics." Cytokine & Growth Factor Reviews, v.21:185-95.*
Abbas-Terki T et al: "Lentiviral-mediated RNA interference", Human Gene Therapy, Mary Ann Li Ebert, New York ,NY, US, vol. 13. No. 18, Dec. 10, 2002 (Dec. 10, 2002), pp. 2197-2201.
Database Biosis [Online] Biosciences Information Service, Philadelphia, PA, US; 1996, Maxwell I H et al: "Autonomous parvovirus transduction of a gene under control of tissue-specific or inducible promoters", Gene Therapy, 1996, 3, pp. 28-36.
Wang Z, Rao DD, Senzer N, & Nemunaitis J Pharm Res., 2011, 28: pp. 2983-2995.
Gartel AL & Kandel ES (2006) Biomol Eng 23, pp. 17-34.
Takeshita F & Ochiya T (2006) Cancer Sci 97, pp. 689-696.
Snove O, Jr. & Rossi JJ (2006) Nat Methods 3, pp. 689-695.
Grimm D, Pandey K, & Kay MA (2005) Methods Enzymol 392, pp. 381-405.
Grimm D & Kay MA ( 2007) Hematology Am Soc Hema tol Educ Program, pp. 473-481.
Power AT & Bell JC (2007) Mol Ther 15, pp. 660-665.
Cotmore SF & Tattersall P (2007) Adv Virus Res pp. 70, 232.
Cornelis JJ, Lang SI, Stroh-Dege AY, Balboni G, Dinsart C, & Rommelaere J (2004) Curr Gene Ther 4, pp. 249-261.
Ohshima T, Iwama M, Ueno Y, Sugiyama F, Nakajima T, Fukamizu A, & Yagami K (1998) J Gen Viral 79 ( Pt 12), 3067-3071.
Rayet B, Lopez-Guerrero JA, Rommelaere J, & Dinsart C (1998) J Viral 72, pp. 8893-8903.
Ueno Y, Harada T, Iseki H, Ohshima T, Sugiyama F, & Yagami K (2001) J Viral 75, pp. 3965-3970.
Ran Z, Rayet B, Rommelaere J, & Faisst S (1999) Virus Res 65, pp. 161-174.
Di Piazza M, Mader C, Geletneky K, Herrero YCM, Weber E, Schlehofer J, Deleu L, & Rommelaere J (2007) J Viral 81, pp. 4186-4198.
Faisst S, Faisst SR, Dupressoir T, Plaza S, Pujol A, Jauniaux JC, Rhode SL, & Rommelaere J (1995) J Viral 69, pp. 4538-4543.
El-Andaloussi N, Ende le M, Zolotukhin I, Potter M, & Muzyczka N (1999) Gene Leuchs B, Kleinschmidt J, Rommelaere J, & Marchini A (2011) Bonifati S, Cancer Gene Ther 18, pp. 240-249.
International Preliminary Report on Patentability in corresponding PCT Application No. PCT/EP2013/000224, dated Jan. 15, 2014.
International Search Report and Written Opinion in corresponding PCT Application No. PCT/EP2013/000224, dated Apr. 9, 2013.
Petrocca F & Lieberman. "Promise and Challenge of RNA Interference-Based Therapy for Cancer." J Clin Oncol 29, pp. 747-754. Feb. 2011, American Society of Clinical Oncology.
Pecot CV, Calin GA, Coleman RL, Lopez-Berestein G, & Sood AK. RNA interference in the clinic: challenges and future direction. Nat Rev Cancer 11, pp. 59-67. Jan. 2011, MacMillan Publishers Limited.

(Continued)

*Primary Examiner* — Jennifer Pitrak McDonald
(74) *Attorney, Agent, or Firm* — Leason Ellis LLP

(57) ABSTRACT

Described are methods for efficiently down regulating the expression of a gene of interest in a cell by use of a modified rodent parvovirus that contains an expressible target specific nucleic acid, preferably an shRNA expression cassette. Also described are cells or organisms comprising said parvovirus.

5 Claims, 5 Drawing Sheets

Specification includes a Sequence Listing.

(56) References Cited

OTHER PUBLICATIONS

Sliva K & Schnierle BS. Selective gene silencing by viral delivery of short hairpin RNA. Viral J 7:248 (p. 1-11). Sep. 2010. BioMed Central.
Rommelaere J, Geletneky K, Angelova Dinsart C, Kiprianova I, Schlehofer JR, & Raykov Z. "Oncolytic parvoviruses as cancer therapeutics." Cytokine Growth Factor Rev 21, pp. 185-195. Apr.-Jun. 2010.
Kestler J, Neeb B, Struyf S, Van Damme J, D'Abramo A, Tattersall P, Rommelaere J, Dinsart C, Cornelis JJ. "*cis* Requirements for the Efficient Production of Recombinant DNA Vectors Based on Autonomous Parvoviruses." Hum Gene Ther 10, pp. 1619-1632. Jul. 1, 1999.
Zolotukhin S, Byrne BJ, Mason E, Zolotukhin I, Potter M, Chesnut K, Summerford C, Samulski RJ, Muzyczka. Gene Ther 6, pp. 973-985. Jun. 1999.

* cited by examiner

Plaque assay

H-1PV sil    H-1PV wt

Cytotoxicity shRNA expression

MODIFIED PARVOVIRUS USEFUL FOR GENE SILENCING

CROSS-REFERENCE TO RELATED PATENT APPLICATIONS

This application is a U.S. National Phase Application under 35 U.S.C. § 371 of International Patent Application No. PCT/EP2013/000224, filed Jan. 25, 2013, and claims the priority of European Patent Application No. 12000554.1, filed Jan. 2, 2012, all of which are incorporated by reference in their entireties. The International Application was published on Aug. 1, 2013 as International Publication No. WO 2013/110464.

INCORPORATION-BY-REFERENCE OF SEQUENCE LISTING

A sequence listing, created on Aug. 4, 2017 as the ASCII text file "10046-003657-US0_SeqListing_v3.txt" having a file size of 15 kilobytes, is incorporated herein by reference in its entirety.

The present invention relates to methods for efficiently down regulating the expression of a gene of interest in a cell. To this end, the present invention provides a modified rodent parvovirus, replication competent, for down regulating a target gene characterized in that said parvovirus contains an expressible target specific nucleic acid, preferably a shRNA expression cassette. The present invention also provides cells or organisms comprising said parvovirus.

RNA interference (RNAi) has not only revolutionized the process of identifying and functionally characterizing new genes, but represents a promising therapeutic option for treating human diseases, in particular cancer (1, 2). The reason of this success lies in the high specificity and effectiveness of RNAi-inducing molecules to target genes that conventional therapeutics cannot reach. Small RNAs such as microRNAs (miRNAs) or small interfering RNAs (siRNAs) have the ability to bind to complementary mRNA sequences triggering their degradation or blocking their translation (1). siRNAs can be designed to silence the expression of any gene, expanding the possibilities of intervention theoretically to the entire genome. For cancer, siRNAs (and miRNAs) have already been proven to be a powerful tool in down-regulating the expression of genes controlling cell signaling, proliferation, differentiation, apoptosis and senescence (1, 2). This list also includes transcription factors generally not manipulable by conventional approaches. Effective silencing of mutated oncogenes or antiapoptotic genes such as K-Ras, mutated p53, c-myc, Her2/neu, bcl-2, bcr-abl, survivin and human papillomavirus 16 E6 leading to cellular arrest and/or apoptosis are only few examples of the success of such approach in cancer therapy at the preclinical level [for a review see (3) and (4)].

The RNAi pathway is found in many eukaryotes including animals and is initiated by the enzyme Dicer, which cleaves long double-stranded RNA (dsRNA) molecules into short fragments of ~20 nucleotides that are called siRNAs. Each siRNA is unwound into two single-stranded ssRNAs, namely the passenger strand and the guide strand. The passenger strand will be degraded, and the guide strand is incorporated into the RNA-induced silencing complex (RISC). The most well-studied outcome is post-transcriptional gene silencing, which occurs when the guide strand base pairs with a complementary sequence of a messenger RNA molecule and induces cleavage by Argonaute, the catalytic component of the RISC complex. In some organisms this process is known to spread systemically despite the initially limited molar concentrations of siRNA.

Despite its great potential several hurdles must be overcome to successfully introduce RNAi-based therapies into the clinic. These include the avoidance of unwanted off-targets effects, activation of the innate immunity and short half-life of the siRNA molecules with knock-down potential diluted every round of cell division (5). However, the major obstacle remains the safe and efficient delivery of RNAi triggering molecules into the target cells resulting in poor cellular uptake and non-specific accumulation in tissues (2, 5).

Short hairpin RNAs (shRNAs) are another class of RNAi effectors (6). shRNAs are transcribed in the nucleus from an expression vector bearing an shRNA expression cassette usually composed of a RNA-Polymerase II (Pol II) or III (Pol III) promoter and a short double-stranded DNA sequence with a hairpin loop. The shRNA transcript is then exported in the cytoplasm and is processed like any siRNA (5, 6). shRNAs are constantly synthesized in host cells, leading to more durable gene silencing. However, intracellular delivery of the shRNA expressing vectors through transfection is poorly efficient, calling for new ways of delivering (6). For this purpose, numerous studies have been directed towards the exploitation of viruses as transfer vehicle for shRNA. This is also favoured by the fact that the shRNA cassettes are usually small in size and can be generally inserted into any viral genome without affecting the packaging capacity of the virus. Examples of virions engineered to this end are based on retrovirus, lentivirus, adenovirus, Herpes Simplex Virus, Vaccinia Virus and Poliovirus (7). These viruses are normally human pathogens, thus they are rendered replication-defective through genetic modifications of their genomes. This makes them unable to spread through the tumour. A replication-defective lentiviral vector that has inserted a shRNA cassette and is used for gene silencing is described by Abbas-Terki et al. (24). Inability to propagate is also found for the Adeno Associated Viruses (AAV) which are commonly used in gene and cancer therapy and also explored as candidate for the delivery of shRNAs (8, 9). Maxwell et al. describe a replication-defective parvovirus LuIII with an engineered P4 promoter expressing luciferase (25). Their vector is replication-defective due to the modification of the P4 promoter and/or expressing a heterologous transgene by deleting other parts of the parvovirus genome. It is also important to mention that for many of the viruses cited above previous exposure of humans to viral infection eliciting protective neutralizing antibodies may jeopardize the virus-based treatment (10).

Therefore, it is the object of the present invention to provide means for efficiently down regulating the expression of a desired gene in a cell or organism.

According to the invention this is achieved by providing the subject matters defined in the claims.

The present invention describes the first autonomous parvovirus carrying an shRNA expression cassette (named H-1PV-silencer). Rodent parvoviruses such as rat parvovirus H-1PV and its mouse homolog minute virus of mice (MVM) have attracted high attention for their anti-cancer potential because they are non pathogenic for humans and possess oncolytic and oncosuppressive properties (11). Pre-existing anti-viral immunity is usually not a problem for these viruses as humans are normally not exposed to rodent parvovirus infection. The parvovirus genome consists of a single stranded DNA of approximately 5100 bases containing two promoters, P4 and P38 which regulate the expression of the non-structural (NS1 and NS2) and capsid (VP1 and VP2) proteins, respectively. Activation of the P4 promoter is a critical step in the PV life cycle. The activity of the P4 promoter is later modulated by its own gene product NS1, but its initial activation is completely dependent on host cellular factors, which are mainly expressed during the S phase of the cell cycle (12). This dependence, together with the fact that the virus is unable to stimulate quiescent cells to proliferate, contributes to the oncotropism of the virus, which replicates preferentially in proliferating, transformed or malignant cells. In addition, parvovirus cytotoxicity is also stimulated by cellular changes associated with neoplastic transformation (11, 13). NS1 is the major viral toxic protein (13). H-1PV has been shown to activate several death pathways in cancer cells. In particular, depending on cell type and growth conditions, H-1PV is able to induce apoptosis (14-16), necrosis (17) or cathepsin B-dependent cell death (18). Although the anticancer potential of PVs is supported by a large set of preclinical studies, efficacy can be expected to be a limiting factor in clinical applications. It is possible that some cancer cells survive virus treatment, causing tumour relapse. The mere fact that these viruses have been isolated from growing tumors, indicates that alone they are not always potent enough to arrest the growth or cause the complete regression of neoplastic lesions (13).

During the experiments resulting in the present invention it could be shown that the insertion of an shRNA cassette at a particular site of the parvovirus genome is compatible with parvovirus packaging capacity and does not interfere with viral replication and cytotoxicity. The virus expresses high levels of shRNAs and is very efficient in gene silencing. The big advantage of H-1PV-silencer in comparison with replication defective vectors resides in its capacity to replicate and propagate in proliferating cells, e.g., cancer cells. Every infected/transduced cell theoretically could become a producer of novel viral particles. Progeny virions through second rounds of infection could spread through the tumour and efficiently delivery and express therapeutic shRNAs. In this setting, the silencing signal could be amplified beyond the initial inoculum. Together, parvovirus-based vectors and shRNA technology compensate each other limitations: the natural oncotropism of parvovirus should specifically and effectively deliver to and mediate transduction of the shRNAs in proliferating cells, e.g., cancer cells, and the shRNA on the other hand should empower the viruses in killing virus less sensitive (cancer) cells. This invention paves the way for the development of novel therapeutic strategies for treating diseases like cancer which combine the powerful anticancer properties of rodent parvovirus and RNAi triggering molecules.

In summary, the rodent parvovirus of the present invention in comparison with other vectors currently in use for the delivery/expression of shRNAs (e.g. lentiviral or AAV based vectors) maintains its capacity to replicate and propagate in cancer cells. As explained in more detail below, every infected/transduced cell theoretically can become a producer of novel viral particles. Progeny virions through second rounds of infection can spread through the tumour and efficiently deliver and express therapeutic shRNAs. In this setting, the silencing signal is amplified beyond the initial inoculum. With the other vectors in use (including the vectors described in (24) and (25)) this is not possible because they are replication defective. The most important advantage of the present invention is that the claimed rodent parvovirus is able to express shRNAs at high levels and is replication competent. In the vector of the present invention the promoter has not been modified and/or a heterologous transgene is expressed by deleting other parts of the parvovirus genome (e.g. the VP region). In the present invention the shRNA expressing cassette is inserted without altering other elements of the parvoviral genome. A new virus has been created that similar to the wild type virus maintains the capacity to package, multiply and spread in cancer cells. A new function (i.e. the capacity to express shRNA) without losing other features of the virus has been created.

HEK 293T cells were transfected with the indicated DNAs. After 12 h the cells were infected with Ad5-GFP and grown for additional 48 h before to be analyzed by fluorescence microscopy for GFP intensity. The bars represent the mean value of a typical experiment performed in triplicate with relative standard deviation. GFP intensity was quantified using the ImageJ software using five different images each containing at least 200 cells (23).

Figure 3:
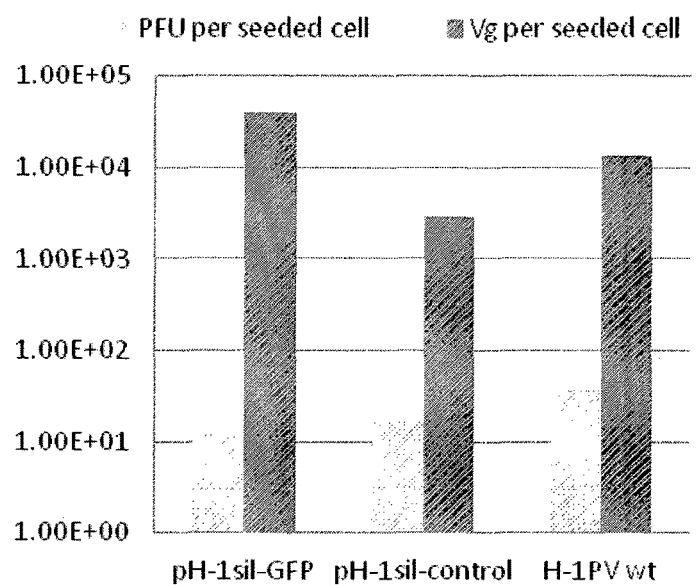
Figure 3:
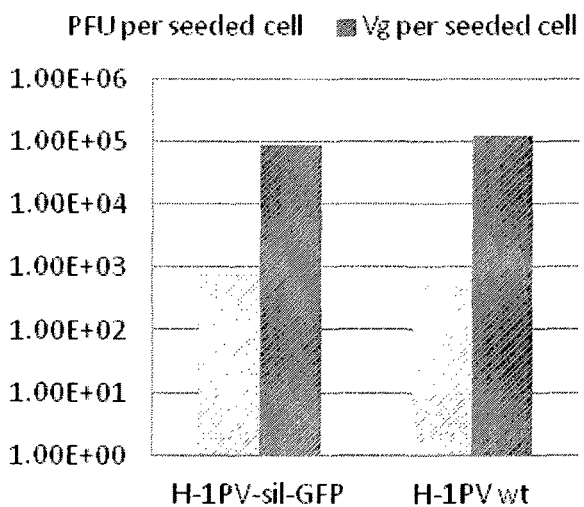
Figure 3:
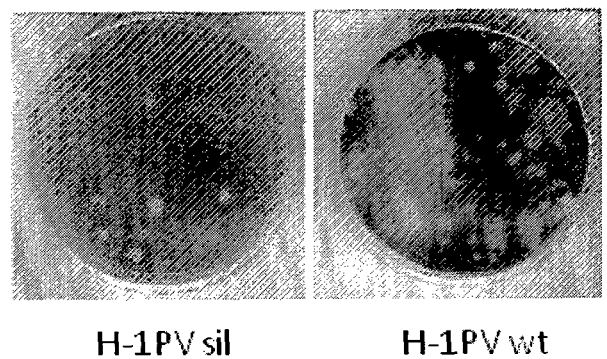

FIG. 3: Production of H-1PV silencer (A) Virus production. Viruses were produced according to the protocol described in Example 1. After viral purification, virus titers were quantified by real time qPCR and plaque assays.

(B) Example of viral amplification through infection. NB324K cells were infected with the indicated viruses. After 5 days, cells were lysed, viruses purified from cell extracts and virus titres quantified by real time qPCR and plaque assays.

(C) Example of plaque assay using the H-1PV wt and H-1PV-sil-GFP.

Figure 4:
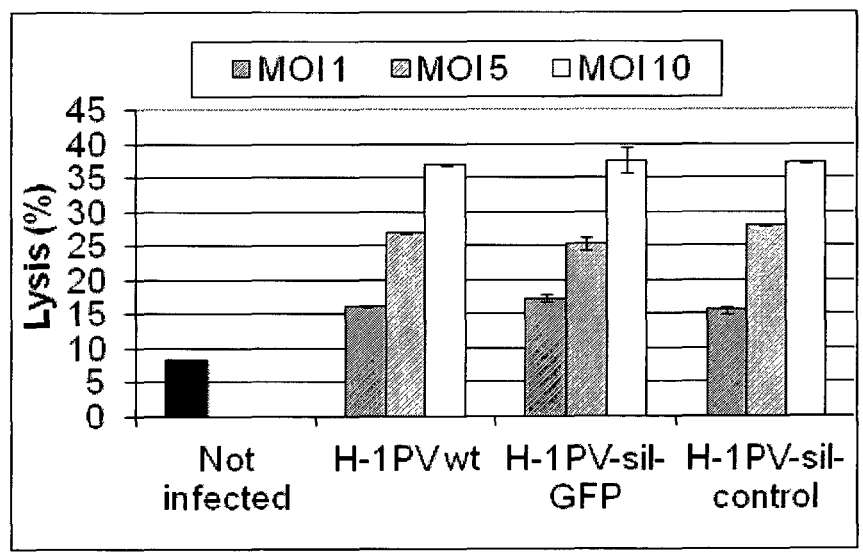

FIG. 4: Intrinsic H-1PV cytotoxicity is not impaired after the insertion of the RNAi cassette NB324K cells were tested for their sensitivity to virus infection by LDH assay. Viruses were used at MOI 1, 5 and 10 for the infection. LDH measurement was performed after 72 h from infection.

Figure 5:
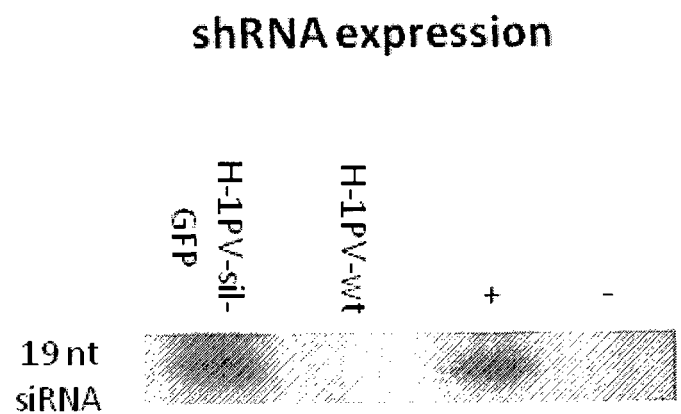
Figure 5:
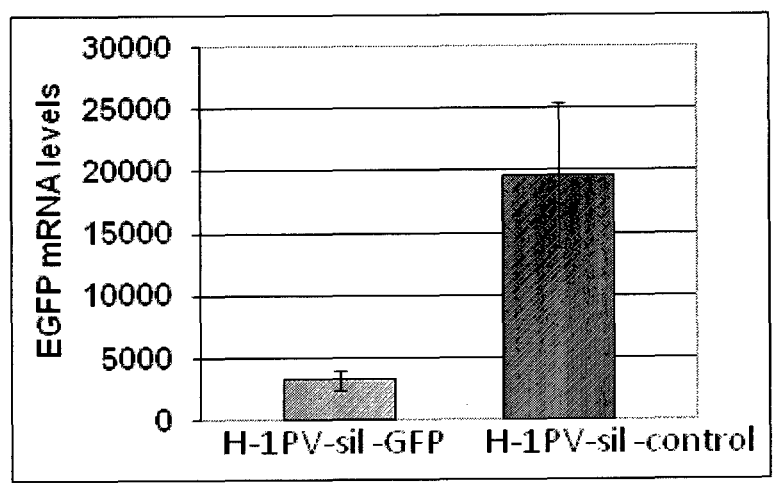
Figure 5:
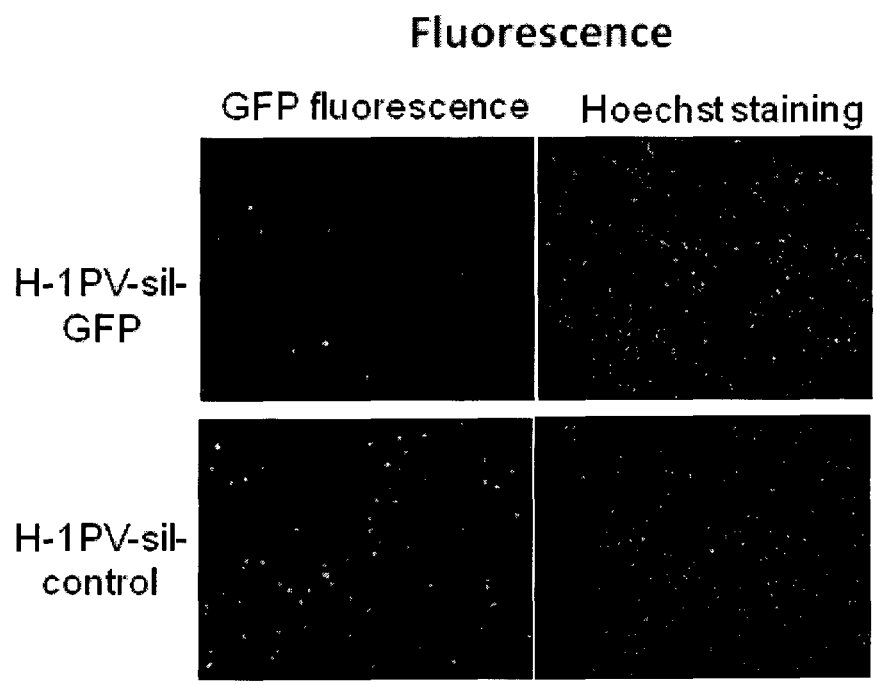
Figure 5:
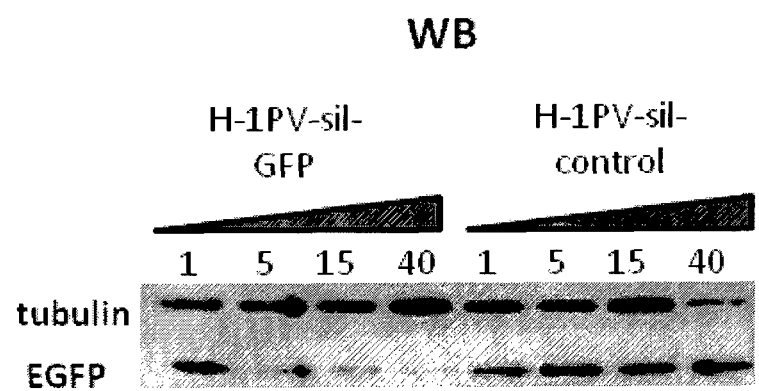

FIG. 5: Efficient gene silencing achieved by using H-1PV silencer (A) shRNA content. shRNAs were extracted from virus infected or plasmid transfected cells and detected using the mirVana miRNA Detection Kit according to the instruction manual. +=positive control: cells transfected with pSilencer 3.1-GFP; −=negative control: cells transfected with pSilencer3.1-control.

(B) qRT-PCR. Isolation of total RNAs from virus infected cells and cDNA synthesis were performed according to the protocols described in Example 1. qRT-PCRs were performed using EGFP and GAPDH (used as housekeeping gene) specific primer sets.

(C) Fluorescence microscopy analysis: example of a representative image. Cells were infected with H-1-sil-GFP and H-1-sil-control and then super-infected with Ad-GFP. After 72 hours cells were analyzed by fluorescence microscopy GFP signal. Hoechst staining was used for nuclei visualization.

(D) Western blotting analysis. NB324K cells were infected with H-1-sil-GFP and H-1-sil-control at the indicated MOIs. 12 hours later, cells were super-infected with Ad-GFP. EGFP protein content was analyzed by SDS-PAGE on total cellular extracts from these cell cultures. β-tubulin was used as a loading control.

Thus, the present invention provides a rodent parvovirus for down regulating the expression of a target gene in a cell characterized in that it contains a target specific nucleic acid in an untranslated region of the parvovirus genome under the control of a promoter or promoter region recognizable by an RNA polymerase in the cell, wherein the transcript of said target specific nucleic acid is an RNAi.

The target specific nucleic acid is inserted in such a way that viral replication and cytotoxicity are not affected.

Preferably, the target specific nucleic acid is inserted downstream of the parvovirus VP gene encoding the capsid proteins of the parvovirus.

The term "parvovirus" as used herein comprises wild-type viruses, replicating viruses and modified replication-competent derivatives thereof, CPG-armed viruses as well as related viruses or vectors based on such viruses or derivatives. Suitable parvoviruses, derivatives, etc. which are useful for therapy, are readily determinable within the skill of the art based on the disclosure herein, without undue empirical effort. Viruses that are capable of replicating and propagating in the host cell are preferred for the present invention.

The term "target gene" as used herein is taken to refer to any nucleic acid of interest which is present in a cell of an animal, fungus or protist. The target gene may be transcribed into a biologically active RNA or it may be part of a larger RNA molecule of which other parts are transcribed into a biologically active RNA. The target gene may be an endogenous gene, it may be a transgene that was introduced through human intervention in the ancestors of the cell, or it may be a gene introduced into the cell by an infectious or pathogenic organism. The target gene may also be of viral origin. Furthermore, the sequence that is targeted may be selected from translated or non-translated regions or intron or preferably exon regions, that is, the coding region, or the 5'UTR or 3'UTR, or a combination of any or all of these.

The target gene used in the present invention may cause a disease in an organism or be involved in causing the disease and is a gene where reduction of the particular gene expression is required to prevent or alleviate the disease. The biological processes affected by the disease that may be reversed by down-regulation of the specific gene target include cell proliferation, cell migration or metastasis, apoptosis, stress signalling, and cell attachment. The target gene (s) may encode enzymes, transcription factors, cytokines, growth factors, cell adhesion or motility factors, cell cycle factors, tumour suppressors, or cell cycle inhibitors.

The term "target specific nucleic acid" as used herein refers to a nucleic acid comprising at least 15, 20, 25, 50, 100 or 200 consecutive nt having at least about 75%, particularly at least about 80%, more particularly at least about 85%, quite particularly about 90%, especially about 95% sequence identity with the complement of a transcribed nucleotide sequence of the target gene.

In the present invention a target gene can be down regulated in an in vivo cell or an in vitro cell. The cell may be a primary cell or a cell that has been cultured for a period of time or the cells may be comprised of a cultured cell line. The cell may be a diseased cell, such a cancer cell or tumor or a cell infected by a virus. The cell may be a stem cell which gives rise to progenitor cells, more mature, and fully mature cells of all the hematopoietic cell lineages, a progenitor cell which gives rise to mature cells of all the hematopoietic cell lineages, a committed progenitor cell which gives rise to a specific hematopoietic lineage, a T lymphocyte progenitor cell, an immature T lymphocyte, a mature T lymphocyte, a myeloid progenitor cell, or a monocyte/macrophage cell. The cell may be a stem cell or embryonic stem cell that is omnipotent or totipotent. The cell maybe a nerve cell, neural cell, epithelial cell, muscle cell, cardiac cell, liver cell, kidney cell, stem cell, embryonic or foetal stem cell or fertilised egg cell.

Thus, in a preferred embodiment of the present invention, the target gene is a disease causing gene, e.g., a pathogenic animal virus gene, a cancer-related gene, an oncogene, anti-apoptotic gene, a gene critical for tumour cell growth, metastasis, angiogenesis or chemioresistance, an immunomodulatory gene, or a gene encoding a cytokine, growth factor, enzyme or transcription factor.

The target gene may be, e.g., a gene from a pathogenic animal virus, for example human immunodeficiency virus (HIV), herpes simplex virus-1 (HSV-1), HSV-2, cytomegalovirus (CMV), a hepatitis virus such as hepatitis B, hepatitis C or hepatitis D viruses, papillomaviruses, RNA viruses such as polio viruses, VSV, Influenza virus, morbillivirus, or a double-stranded RNA virus such as a reovirus. The virus may be pathogenic to animals other than humans, for example Foot and Mouth Virus, Rinderpest virus, Blue tongue virus, Swine Fever virus, Porcine circa virus, Capripox virus, West Nile Virus, Henipah virus, Marek's Disease Virus, Chicken Aneamia Virus, Newcastle Disease Virus, Avian Influenza virus, Infectious Bursal Disease Virus, Aquaculture viruses such as iridoviruses, paramyxoviruses or White Spot Syndrome Virus.

Preferably, said rodent parvovirus is formulated as a pharmaceutical composition, wherein the parvovirus is present in an effective dose and combined with a pharmaceutically acceptable carrier. "Pharmaceutically acceptable" is meant to encompass any carrier which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Additional pharmaceutically compatible carriers can include gels, bioasorbable matrix materials, implantation elements containing the parvovirus (therapeutic agent), or any other suitable vehicle, delivery or dispensing means or material(s). Such carriers can be formulated by conventional methods and can be administered to the subject at an effective dose.

An "effective dose" refers to amounts of the active ingredients that are sufficient to effect treatment. An "effective dose" may be determined using methods known to one skilled in the art (see for example, Fingl et al., The Pharmocological Basis of Therapeutics, Goodman and Gilman, eds. Macmillan Publishing Co., New York, pp. 1-46 ((1975)).

Administration of the parvovirus may be effected by different ways, e.g. by intravenous, intratumoral, intraperetoneal, subcutaneous, intramuscular, topical or intradermal administration. The route of administration, of course, depends on the kind of therapy. Preferred routes of administration are intravenous (i.v.), intratumoral or endobronchial administration. If infectious virus particles are used which have the capacity to penetrate through the blood-brain barrier, treatment could be performed or at least initiated by intravenous injection of, e.g., H1 virus.

The dosage regimen of the parvovirus is readily determinable within the skill of the art, by the attending physician based an patient data, observations and other clinical factors, including for example the patient's size, body surface area, age, sex, the particular modified parvovirus etc. to be administered, the time and route of administration, the type of mesenchymal tumor, general health of the patient, and other drug therapies to which the patient is being subjected.

As another specific administration technique, the parvovirus can be administered to the patient from a source implanted in the patient. For example, a catheter, e.g., of silicone or other biocompatible material, can be connected to a small subcutaneous reservoir (Rickham reservoir) installed in the patient, e.g., during tumor removal, or by a separate procedure, to permit the parvovirus to be injected locally at various times without further surgical intervention. The parvovirus can also be injected into a tumor by stereotactic surgical techniques or by neuronavigation targeting techniques.

Administration of the parvovirus can also be performed by continuous infusion of viral particles or fluids containing viral particles through implanted catheters at low flow rates using suitable pump systems, e.g., peristaltic infusion pumps or convection enhanced delivery (CED) pumps.

As yet another method of administration of the parvovirus is from an implanted device constructed and arranged to dispense the parvovirus to the desired tissue. For example, wafers can be employed that have been impregnated with the parvovirus, e.g., parvovirus H1, wherein the wafer is attached to the edges of the resection cavity at the conclusion of surgical tumor removal. Multiple wafers can be employed in such therapeutic intervention. Cells that actively produce the parvovirus, e.g., parvovirus H1, can be injected into the tumor, or into the tumor cavity after tumor removal.

In a further preferred embodiment of the present invention, the rodent parvovirus is parvovirus H1 (H1PV) or a related parvovirus such as LuIII, Mouse minute virus (MMV), Mouse parvovirus (MPV), Rat minute virus (RMV), Rat parvovirus (RPV) or Rat virus (RV).

In a particularly preferred embodiment of the present invention, the target specific nucleic acid is inserted at nucleotide 4683 of the wild type H-1PV genome. However the insertion of the cassette in other regions of parvovirus genome is also considered as well as other RNAi triggering molecules such as microRNAs and/or antisense oligonucleotides. In a further particularly preferred embodiment of the present invention, the promoter or promoter region recognizable by RNA polymerases is a RNA-polymerase II (Pol II) promoters such as for instance CMV and human ubiquitin C or RNA-polymerase III (Pol III) promoters such as U6, H1, 7SK and tRNA. An example of a particularly preferred RNA-polymerase III (Pol III) promoter is the RNA-polymerase III H1 promoter.

In a further particularly preferred embodiment of the present invention, the target specific nucleic acid is an shRNA. An shRNA is a small hairpin RNA or short hairpin RNA that is a sequence of RNA that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the shRNA that is bound to it.

In a further particularly preferred embodiment of the present invention, the target specific nucleic acid, e.g., shRNA, has a length of at least 15 nucleotides.

The present invention also relates to a rodent parvovirus as characterized above for use in treating a disease caused by a pathogenic animal virus gene, a cancer-related gene, an oncogene, anti-apoptotic gene, a gene critical for tumour cell growth, metastasis, angiogenesis or chemioresistance, or a disease associated with the aberrant expression of an immunomodulatory gene or a gene encoding a cytokine, growth factor, enzyme or transcription factor.

In a preferred embodiment, said parvovirus can be used for treating a tumour, preferably for treating a brain tumor.

In a further preferred embodiment, said parvovirus can be used for the treatment of a tumour characterized in that the cells of said tumour are resistant to chemotherapy and/or radiotherapy.

Patients treatable by the parvovirus according to the invention include humans as well as non-human animals. Examples of the latter include, without limitation, animals such as cows, sheep, pigs, horses, dogs, and cats.

The present invention also provides a cell of an animal, fungus or protist comprising a parvovirus as hereinbefore described. In an embodiment, the cell is in vitro. The cell is preferably an animal cell, an isolated human cell, an in vitro human cell, a non-human vertebrate cell, a non-human mammalian cell, fish cell, cattle cell, goat cell, pig cell, sheep cell, rodent cell, hamster cell, mouse cell, rat cell, guinea pig cell, rabbit cell, non-human primate cell, nematode cell, shellfish cell, prawn cell, crab cell, lobster cell, insect cell, fruit fly cell, Coleapteran insect cell, Dipteran insect cell, Lepidopteran insect cell or Homeopteran insect cell.

Finally, the present invention also provides a transgenic, non-human animal, fungus or protist comprising a parvovirus as hereinbefore described. Transgenic animals can be produced by the injection of the parvovirus into the pronucleus of a fertilized oocyte, by transplantation of cells, preferably uindifferentiated cells into a developing embryo to produce a chimeric embryo, transplantation of a nucleus from a recombinant cell into an enucleated embryo or activated oocyte and the like. Methods for the production of trangenic animals are well established in the art and, e.g., described in U.S. Pat. No. 4,873,191.

The below examples explain the invention in more detail.

EXAMPLE 1

Materials and Methods (A) Cell Culture

NB324K and HEK293T cells were grown in Minimum Essential Medium (MEM) and Dulbecco's Modified Eagle Medium (DMEM) (Sigma-Aldrich, Munich, Germany) respectively, supplemented with 5 (MEM) or 10% (DMEM) Foetal Calf Serum, 100 units/ml penicillin, 100 μg/ml streptomycin and 2 mM L-Glutamine (all from Gibco, Invitrogen, Karlsruhe, Germany). All cells were kept at 37° C. in a 5% $CO_2$ atmosphere, 95% humidity.

(B) Plasmid Construction

The Pol III H1 shRNA expression cassette was cloned into the pSR19 (19) and ΔpSR19 (20) plasmids. The former contains the entire H-1PV wt genome and the latter a deleted version lacking the nucleotides 2022-2135 (encoding for the C-terminus region of parvoviral NS2 protein). The HPAI restriction enzyme site (nucleotides 4687-4693 according to the NCBI reference sequence NC_001358.1) was used for the cloning. The cassette was amplified by PCR using as template DNA the pSilencer 3.1 vector (Ambion, Life Technologies, Grand Island, N.Y., USA) and the following primers For H1 POL III 5'-GTTAACGAATTCATATTTG-CATGT-3'-(SEQ ID NO: 1) and REV H1 POL III 5'-GTTAACGCGGCCGCGGATCCGAGTGGTCTCATACAGAAC-3' (SEQ ID NO. 2). The cassette contains the BamH1-NotI unique restriction sites for an easy cloning of the shRNAs into the plasmid. The two plasmids were named pH-1PV-silencer 1 and pH-1PV-silencer 2. For the cloning of the shRNA the following pairs of oligonucleotides were used: shRNA EGFP Top strand 5'-GATCCGCTGGAGTACAACTACAACTTCAAGAGAGTTGTAGTTGTACT CCAGCTTTTTTGGAAGC-3' (SEQ ID NO: 3) and shRNA-EGFP bottom strand 5'-GGCCGCTTCCAAAAAAGCTGGAGTACAACTACAACTCTCTTGAAGTTGTAGT TGTACTCCAG CG-3'(SEQ ID NO: 4); shRNA negative control top strand 5'-GATCCACAGCAGAGCAGATCGTTCTTCAAGAGAGAACGATCTGCTCTGCTGT TTTTGGAAGC-3' (SEQ ID NO: 5)and shRNA negative control bottom strand 5' GGCCGCTTCCAAAAACAGCAGAGCAGATCGTTCTCTCTTGAAGAACGATCTG CTCTGCTGTG-3'(SEQ ID NO: 6). Oligonucleotides were annealed at 96° C. and directly cloned into previously digested BamH1-NotI pH-1PV silencer 1 and 2 plasmids. A similar approach was also used for the cloning of the shRNAs into the pSilencer 3.1-H1 puro vector (Ambion). In this case the BamHI/HindIII restriction sites and the following overlapping oligonucleotides were used: shRNA-EGFP Ambion top strand: 5'-GATCCGCTGGAGTACAACTACAACTTCAAGAGAGTT GTAGTTGTACTCCAGCTTTTTTGGAAA-3' (SEQ ID NO: 7) and shRNA-EGFP Ambion bottom strand 5'-AGCTTTTCCAAAAAAGCTGGAGTACAACTACAACTCTCTTGAAGTTGTAGTTG TACTCCAGCG-3' (SEQ ID No: 8); shRNA negative control top strand Ambion 5'-GATCCACAGCAGAGCAGATCGTTCTTCAAGAGAGAACGATCTGCTCTGCTGT TTTTGGAAA-3' (SEQ ID NO: 9)and shRNA negative control bottom strand Ambion 5'-AGCTTTTCCAAAAACAGCAGAGCAGATCGTTCTCTCTTGAAGAACGATCTG CTCTGCTGTG-3' (SEQ ID NO: 10). All clones were propagated in *Escherichia coli* strain SURE (Invitrogen, Darmstadt, Germany) and DNA verified by sequencing.

(C) Virus Production and Titration

All viruses were produced in HEK293T cells. The cells were cultivated in T75 culture flasks and transiently transfected at 12.5% confluency with 4-10 μg/flask of viral plasmid. After 4 days, cells were harvested within their medium and lysed by 3 freeze-and-thaw cycles and cellular debris was removed by centrifugation. Produced viruses were further amplified by infecting NB324K cells and purified through iodixanol gradient centrifugation (21). Viral titration was performed by qPCR and plaque assay according to (22) and expressed either as viral genome (Vg) or plaque-forming unit (PFU) per ml.

(D) Viral Plasmid Transfection

Figure 2:
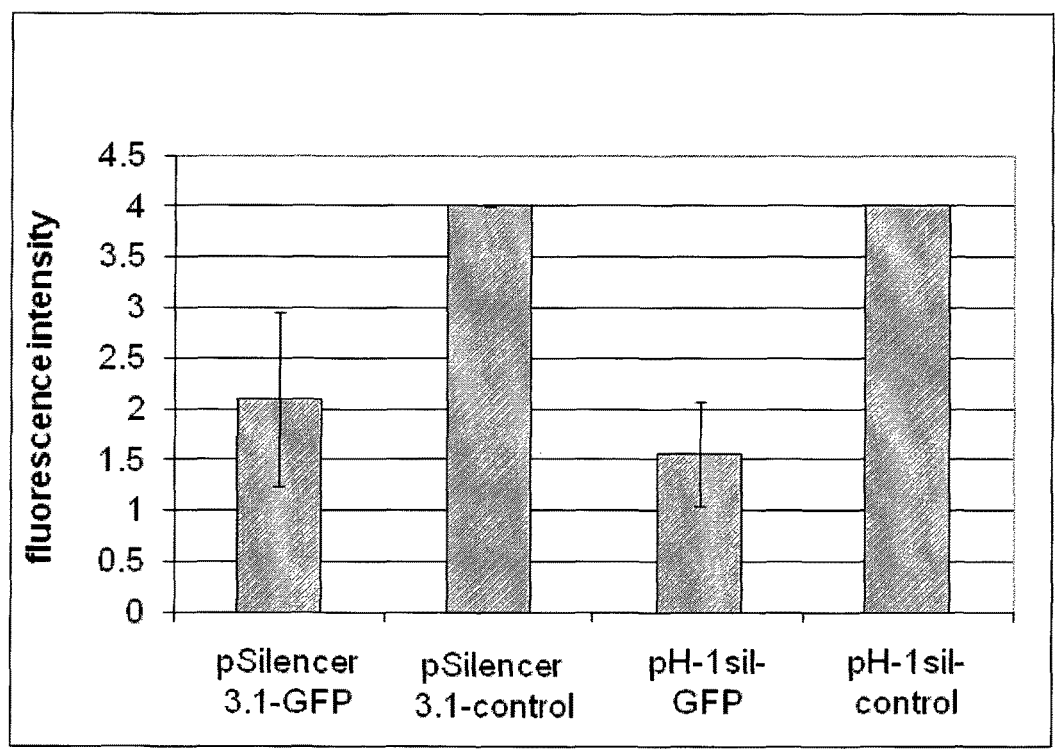
FIG. 2: Efficient gene silencing achieved by using the pH-1PV silencer vector

For the experiment described in FIG. 2, HEK293T cells were grown in a 10 cm dish and transfected at approximately 40% confluence using FuGENE HD (Roche, Mannheim, Germany) according to the manufacturer's instructions. 2 μg of DNA were diluted in serum-free medium to a final concentration of 20 ng/ μl and then 7.5 μl of Fugene were added to the mixture. After 30 min of incubation at room temperature, the mixture was added drop-wise to the cells.

(E) Virus Infection

For the experiments described in FIG. 4, $1.5 \times 10^5$ of NB324K cells were seeded in 6-well plates and incubated overnight before to be infected with H-1PV wt, H-1PV-silencer-GFP or H-1PV-silencer-control, if not differently specified, at the MOI 5 (PFU/cell). 12 hours after infection, cells were super infected with adenovirus, expressing EGFP protein used at MOI 80 green fluorescent transduction units (GFU)/cell and grown for additional 72 hours before to be processed.

(F) LDH Assay

Virus lytic activity was determined by LDH assay (CytoTox 96; Promega, Mannheim, Germany) according to the manufacturer's instructions. NB324K cells were seeded in 96-well plates (2,500 cells/well) in 50 μl of medium. After 24 h, cells were infected by adding additional 50 μl of medium containing the virus at the MOI 5 (pfu/cell). At 72 h post infection, cells were processed for determination of LDH release. Colirimetric changes were measured by using a microtiter reader at 492 nm.

(G) shRNA Extraction and Detection shRNA extraction from parvovirus infected NB324K cells was carried out using the mirVana miRNA Isolation Kit (Ambion, Life technologies, Darmstadt, Germany), according to the manufacturer's protocol. Detection of shRNAs was performed using the mirVana miRNA Detection Kit (Ambion) as described in the instruction manual.

(H) RNA Extraction and cDNA Preparation

Total RNA was isolated from cells using the RNeasy Mini RNA purification kit (Qiagen, Hilden, Germany). cDNA synthesis was performed using the QuantiTect Probe RT-PCR Kit (Qiagen) according to the manufacturer's protocol using random hexamer primers (Promega), with (+RT) or without (−RT) addition of HotStarTaq DNA Polymerase.

(I) Quantitative Real-Time PCR (qRT-PCR)

QRT-PCR was performed using a TaqMan ABI Prism 7600 Sequence detection system (Applied Biosystems, Germany) using Power SYBR Green PCR Master Mix (Applied Biosystems, Germany). To normalize each sample for RNA control, the house keeping gene GAPDH was used as a control gene. PCRs were performed using the following primers: GapdhFor5'-AGCAACTCCCACTCTTCCACCTT-3' (SEQ ID NO: 11), GapdhRev 5'-ACCCTGTTGCTGTAGCCGTATTCAT-3' (SEQ ID NO: 12), EGFPFor 5'-CCACTACCTGAGCACCCAGTC-3' (SEQ ID NO: 13), EGFPRev 5'-CACGAACTCCAGCAGGACCA-3' (SEQ ID NO: 14).

(J) Western Blotting

Cells infected with H-1PV-sil-GFP, H-1PV-sil-control and H-1PV wild type were trypsinized and washed twice with PBS. The cell pellet was lysed in 500 μl of lysis buffer consisting of 50 mM Tris-HCl pH 8, 200 mM NaCl, 0.5% NP-40, 1 mM DTT, 10% glycerol and a mix of protease inhibitors (Roche Diagnostics, Mannheim Germany)) and kept on ice for 20 min. After centrifugation (10,000 rpm×10 min) the supernatant was collected and the protein amount was measured by BCA assay (Perkin Elmer) according to the manufacture's manual. Total cellular extracts (30 μg) were loaded and separated on 12% SDS gels and transferred onto Hypbond-P membrane (GE Healthcare) by wet blotting (Invitrogen, X-Cell Sure Lock). The membranes were blocked in PBS, 0.05% Tween 20, 5% nonfat dry milk for 1 h at RT. The blots were incubated with the following primary antibodies over night at 4° C.: GFP rabbit (Santa Cruz Biotechnologies, Heidelberg, Germany), β-Tubulin mouse (Sigma Life Science, Hamburg, Germany). After membrane washing the peroxidase-conjugated goat anti-rabbit or goat anti-mouse antibody (Santa Cruz Biotechnology, Heidelberg, Germany).) was added for 1 h at room temperature. Membranes were then washed and visualized with the Western Lightning Plus-ECL detection kit (Perkin Elmer, Rodgan, Germany).

(K) Fluorescent Microscopy

NB324K cells were grown in 6-well plates and then infected as described above. After 72 h, cells were washed twice with 1×PBS, fixed with 4% paraformaldehyde (PFA) at 4° C. and washed again with PBS. Nuclei staining was performed using the Hoechst 33342 dye. Fixed cells were examined with Leica DMIL fluorescent microscope. GFP intensity was quantified using the ImageJ software (23).

EXAMPLE 2

Figure 1:
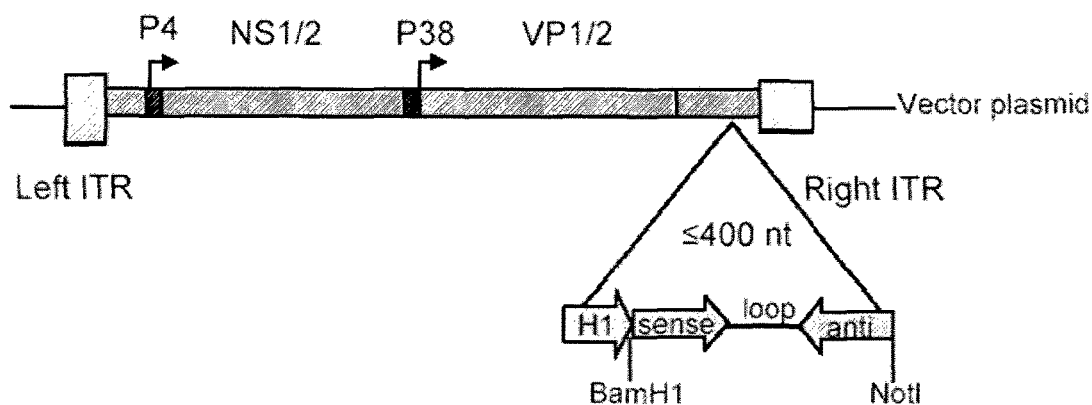
FIG. 1: Schematic representation of pH-1PV silencer containing an shRNA expression cassette The RNAi cassette consisting of the RNA polymerase III H1 promoter was inserted into the non-coding region of the genome downstream the VP gene encoding for the VP1 and VP2 capsid proteins. Unique BamHI and Not I restriction enzymes were inserted for shRNA cloning. Parvoviral P4 and P38 promoters are also illustrated. ITR, inverted terminal repeat. Figure not drawn to scale.

Construction of Replication Competent H-1PV for the Delivery and Expression of shRNAs A strategy to generate replication-competent H-1PV virus harbouring a shRNA expression cassette was conceived. For shRNAs expression the RNA-polymerase III H1 promoter (total size of 170-180 bases) was employed because of the limiting DNA packaging capacity of PVs (max. 300 bp) that would most likely not tolerate the insertion of other cassettes. In order to avoid that the insertion would disrupt any viral ORFS, it was decided to incorporate the cassette into the H-1PV untranslated region downstream of the VP gene (encoding for the capsid proteins), namely at nucleotide 4683 (HpaI restriction enzyme site within the parvovirus genome). Unique restriction sites were introduced to facilitate the shRNAs cloning into the cassette by using annealed oligonucleotides with appropriate overhangs (FIG. 1). Two different parvovirus backbones were used for the insertion of the cassette, the pSR19 containing the full length H-1PV genome (19) and the H-1 dr containing a deletion encompassing the nucleotides 2022-2135 (20). This deletion does not interfere with parvovirus replication and infection of human cells and therefore provides a bit larger genetic space for the insertion of a foreign transgene. The new plasmids were named pH-1PV Silencer 1 and pH-1PV Silencer 2. The results presented here refer to the pH-1PV Silencer 2 (hereafter abbreviated in pH-1sil) but similar results were also obtained using the other plasmid. In order to test the efficacy of the new plasmid to induce gene silencing, shRNAs directed against the gene encoding for the Enhanced Green Fluorescent Protein (EGFP) (pH-1sil-GFP) and control shRNA (a scrambled shRNA sequence that does not recognize any known gene sequence) (pH-1sil-control) were introduced and the two plasmids transiently transfected in HEK293T cells. As positive and negative controls a commercially available plasmid was used, namely the pSilencer 3.1 (Ambion, Austin, Tex., USA) carrying the same EGFP or scrambled shRNAs. 16 hours after transfection, cells were infected with recombinant Ad 5 virus carrying the EGFP gene. Cells were then analyzed under a fluorescence microscope. Similarly to the pSilencer 3.1 plasmid, pH-1sil-GFP was very efficient in silencing EGFP, reducing its expression by more than 60% (FIG. 2).

The two pH-1sil plasmids were used for parvovirus production in comparison with the parental H-1PV plasmid (wt) (pSR19) according to the procedure described in Example 1. Wt and mutant H-1PV viruses were produced at similar titers indicating that the insertion of the cassette did not interfere with the overall fitness of the virus (FIG. 3A). Plaque and LDH assays on NB324K cells confirmed the capacity of the shRNA-containing viruses to replicate and induce cell lysis (FIG. 3B-C and FIG. 4). The new viruses were named H-1PV-sil-GFP and H-1PV-sil-control.

EXAMPLE 3

H-1PV-sil Virus Expresses shRNAs

Next, the ability of H-1PV-sil virus to express shRNAs was demonstrated. NB324K cells were infected with H-1PV-sil-GFP and H-1PV wt (used as a negative control). As a positive control for shRNA expression the cells were transfected with pSilencer 3.1 shRNA-EGFP vector. After 72 hours the cells were analyzed for shRNA-GFP content. High levels of shRNAs were detected in H-1PV-sil-GFP infected cells (FIG. 5A).

EXAMPLE 4

H-1PV-sil Virus is Capable of Knocking down EGFP Expression

Next, the ability of H-1PV-silencer to knock-down the EGFP expression was examined. NB324K cells were infected with H-1PV-sil-GFP or H-1PV-sil-control viruses and 12 hours later super-infected with Ad5 expressing EGFP protein. Cells were grown for additional 72 h before to be processed for RNA extraction. Quantitative real-time PCR showed that expression of EGFP in cells infected with H-1-sil-GFP was dramatically reduced by more than 80% in comparison with the expression found in control viruses (FIG. 5B).

A similar experiment was performed for checking silencing efficiency at the protein level. Immuno fluorescence and Western blot analyses both confirmed that H-1PV-silencer-GFP, but not control virus, was very efficient in silencing EGFP expression and it does in a dose dependent manner (FIGS. 5C and D).

All together these results provide proof of concept that H-1PV or its derivatives can be used as vehicle for the delivery of shRNAs.

LIST OF REFERENCES

1. Petrocca F & Lieberman J *J Clin Oncol* 29, 747-754.
2. Wang Z, Rao D D, Senzer N, & Nemunaitis *J Pharm Res.*
3. Gartel A L & Kandel E S (2006) *Biomol Eng* 23, 17-34.
4. Takeshita F & Ochiya T (2006) *Cancer Sci* 97, 689-696.
5. Pecot C V, Calin G A, Coleman R L, Lopez-Berestein G, & Sood A K *Nat Rev Cancer* 11, 59-67.
6. Snove O, Jr. & Rossi J J (2006) *Nat Methods* 3, 689-695.
7. Sliva K & Schnierle B S *Virol J* 7, 248.
8. Grimm D, Pandey K, & Kay M A (2005) *Methods Enzymol* 392, 381-405.
9. Grimm D & Kay M A (2007) *Hematology Am Soc Hematol Educ Program*, 473-481.
10. Power A T & Bell J C (2007) *Mol Ther* 15, 660-665.
11. Rommelaere J, Geletneky K, Angelova A L, Daeffler L, Dinsart C, Kiprianova I, Schlehofer J R, & Raykov Z (2010) *Cytokine Growth Factor Rev* 21, 185-195.
12. Cotmore S F & Tattersall P (2007) *Adv Virus Res* 70, 183-232.
13. Cornelis J J, Lang S I, Stroh-Dege A Y, Balboni G, Dinsart C, & Rommelaere J (2004) *Curr Gene Ther* 4, 249-261.
14. Ohshima T, Iwama M, Ueno Y, Sugiyama F, Nakajima T, Fukamizu A, & Yagami K (1998) *J Gen Virol* 79 (Pt 12), 3067-3071.
15. Rayet B, Lopez-Guerrero J A, Rommelaere J, & Dinsart C (1998) *J Virol* 72, 8893-8903.

16. Ueno Y, Harada T, Iseki H, Ohshima T, Sugiyama F, & Yagami K (2001) *J Virol* 75, 3965-3970.
17. Ran Z, Rayet B, Rommelaere J, & Faisst S (1999) *Virus Res* 65, 161-174.
18. Di Piazza M, Mader C, Geletneky K, Herrero Y C M, Weber E, Schlehofer J, Deleu L, & Rommelaere J (2007) *J Virol* 81, 4186-4198.
19. Kestler J, Neeb B, Struyf S, Van Damme J, Cotmore S F, D'Abramo A, Tattersall P, Rommelaere J, Dinsart C, & Cornelis J J (1999) *Hum Gene Ther* 10, 1619-1632.
20. Faisst S, Faisst S R, Dupressoir T, Plaza S, Pujol A, Jauniaux J C, Rhode S L, & Rommelaere J (1995) *J Virol* 69, 4538-4543.
21. Zolotukhin S, Byrne B J, Mason E, Zolotukhin I, Potter M, Chesnut K, Summerford C, Samulski R J, & Muzyczka N (1999) *Gene Ther* 6, 973-985.
22. El-Andaloussi N, Endele M, Leuchs B, Bonifati S, Kleinschmidt J, Rommelaere J, & Marchini A (2011) *Cancer Gene Ther* 18, 240-249.
23. Rasband W S (1997-2011.) U.S. National Institutes of Health, Bethesda, Md., USA, http://imagej.nih.gov/ij/.
24. Abbas-Terki, T., Blanco-Bose, W., Déglon, N., Prlaong, W., Aebischer, P., (2002), *Human Gene Therapy* 13, 2197-2201
25. Maxwell, I. H., Spitzer, A. L., Long, C. J., Maxwell, F., (1996), *Gene Therapy* 3, No. 1, 28-36

The invention claimed is:

1. A modified parvovirus having a modified H-1 parvoviral genome comprising a non-coding region downstream of a parvovirus VP gene, wherein the modified H-1 parvoviral genome comprises the nucleotide sequence of SEQ ID NO:15 comprising the following mutations:
   (i) a deletion of nucleotides 2022-2135 of SEQ ID NO:15; and
   (ii) an insertion within the non-coding region downstream of the parvovirus VP gene, wherein the insertion is a nucleic acid molecule encoding a short hairpin RNA (shRNA) transcript under the control of a RNA polymerase III H1 promoter, wherein the shRNA is specific to a target gene,
   and wherein the modified parvovirus is capable of replicating and propagating in a cell autonomously.

2. The modified parvovirus of claim 1, wherein the target gene is a disease-causing gene.

3. The modified parvovirus of claim 2, wherein the disease-causing gene is a pathogenic animal virus gene, a cancer-related gene, an oncogene, anti-apoptotic gene, a gene critical for tumour cell growth, metastasis, angiogenesis or chemioresistance, an immunomodulatory gene, or a gene encoding a cytokine, growth factor, enzyme or transcription factor.

4. A composition comprising the modified parvovirus of claim 1, further comprising a solvent suitable for intravenous (i.v.), intratumoral or endobronchial administration.

5. A cell containing the modified parvovirus of claim 1.

* * * * *

SEQUENCE LISTING

```
<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Primer_fwd H1 POL III

<400> SEQUENCE: 1
gttaacgaat tcatatttgc atgt                                           24

<210> SEQ ID NO 2
<211> LENGTH: 39
<212> TYPE: DNA
<213> ORGANISM: Artificial Sequence
<220> FEATURE:
<223> OTHER INFORMATION: Primer_rev H1 POL III

<400> SEQUENCE: 2
gttaacgcgg ccgcggatcc gagtggtctc atacagaac                           39

<210> SEQ ID NO 3
<211> LENGTH: 64
<212> TYPE: DNA
<213> ORGANISM: Artificial Sequence
<220> FEATURE:
<223> OTHER INFORMATION: Cloning-Primer shRNA EGFP Top strand

<400> SEQUENCE: 3
gatccgctgg agtacaacta caacttcaag agagttgtag ttgtactcca gcttttttgg    60
aagc                                                                 64

<210> SEQ ID NO 4
<211> LENGTH: 64
<212> TYPE: DNA
<213> ORGANISM: Artificial Sequence
<220> FEATURE:
<223> OTHER INFORMATION: Cloning-Primer shRNA EGFP Bottom strand

<400> SEQUENCE: 4
ggccgcttcc aaaaaagctg gagtacaact acaactctct tgaagttgta gttgtactcc    60
agcg                                                                 64

<210> SEQ ID NO 5
<211> LENGTH: 62
<212> TYPE: DNA
<213> ORGANISM: Artificial Sequence
<220> FEATURE:
<223> OTHER INFORMATION: Cloning-Primer shRNA negative control top
      strand
```

<400> SEQUENCE: 5
gatccacagc agagcagatc gttcttcaag agaaacgat ctgctctgct gttttttggaa    60 gc                                                                  62

<210> SEQ ID NO 6
<211> LENGTH: 62
<212> TYPE: DNA
<213> ORGANISM: Artificial Sequence
<220> FEATURE:
<223> OTHER INFORMATION: Cloning-Primer shRNA negative control bottom
      strand

<400> SEQUENCE: 6
ggccgcttcc aaaaacagca gagcagatcg ttctctcttg aagaacgatc tgctctgctg    60
tg                                                                  62

<210> SEQ ID NO 7
<211> LENGTH: 63
<212> TYPE: DNA
<213> ORGANISM: Artificial Sequence
<220> FEATURE:
<223> OTHER INFORMATION: Cloning-Primer shRNA EGFP Ambion top strand

<400> SEQUENCE: 7
gatccgctgg agtacaacta caacttcaag agagttgtag ttgtactcca gcttttttgg    60
aaa                                                                 63

<210> SEQ ID NO 8
<211> LENGTH: 63
<212> TYPE: DNA
<213> ORGANISM: Artificial Sequence
<220> FEATURE:
<223> OTHER INFORMATION: Cloning-Primer shRNA EGFP Ambion bottom strand

<400> SEQUENCE: 8
agcttttcca aaaaagctgg agtacaacta caactctctt gaagttgtag ttgtactcca    60
gcg                                                                 63

<210> SEQ ID NO 9
<211> LENGTH: 61
<212> TYPE: DNA
<213> ORGANISM: Artificial Sequence
<220> FEATURE:
<223> OTHER INFORMATION: Cloning-Primer shRNA neagtive control top
      strand Ambion

<400> SEQUENCE: 9
gatccacagc agagcagatc gttcttcaag agaaacgat ctgctctgct gttttggaa     60 a                                                                   61

<210> SEQ ID NO 10
<211> LENGTH: 61
<212> TYPE: DNA
<213> ORGANISM: Artificial Sequence
<220> FEATURE:
<223> OTHER INFORMATION: Cloning-Primer shRNA negative control bottom
      strand Ambion

<400> SEQUENCE: 10
agcttttcca aaaacagcag agcagatcgt tctctcttga agaacgatct gctctgctgt    60
g                                                                   61

```
<210> SEQ ID NO 11
<211> LENGTH: 23
<212> TYPE: DNA
<213> ORGANISM: Artificial Sequence
<220> FEATURE:
<223> OTHER INFORMATION: Primer_fwd Gapdh

<400> SEQUENCE: 11
agcaactccc actcttccac ctt                                          23

<210> SEQ ID NO 12
<211> LENGTH: 25
<212> TYPE: DNA
<213> ORGANISM: Artificial Sequence
<220> FEATURE:
<223> OTHER INFORMATION: Primer_rev Gapdh

<400> SEQUENCE: 12
accctgttgc tgtagccgta ttcat                                        25

<210> SEQ ID NO 13
<211> LENGTH: 21
<212> TYPE: DNA
<213> ORGANISM: Artificial Sequence
<220> FEATURE:
<223> OTHER INFORMATION: Primer_fwd EGFP

<400> SEQUENCE: 13
ccactacctg agcacccagt c                                            21

<210> SEQ ID NO 14
<211> LENGTH: 20
<212> TYPE: DNA
<213> ORGANISM: Artificial Sequence
<220> FEATURE:
<223> OTHER INFORMATION: Primer_rev EGFP

<400> SEQUENCE: 14
cacgaactcc agcaggacca                                              20

<210> SEQ ID NO 15
<211> LENGTH: 5176
<212> TYPE: DNA
<213> ORGANISM: Parvovirus H1

<400> SEQUENCE: 15 cattttaga actgaccaac catgttcacg caagtgacgt gatgacgcgc gctgcgcgcg     60
ctgccttcgg cagtcacacg tcactagcgt ttcacatggt tggtcagttc taaaaatgat   120
aagcggttca gagagtttga aaccaaggcg ggaaacggaa gtgggcgtgg ctaactgtat   180
ataagcagtc actctggtcg gttactcact ctgctttcat ttctgagttt gtgagacaca   240
ggagcgagac taaccaacta accatggctg gaaacgctta ctccgatgag gttttgggag   300
taacaaactg gctgaaggac aaaagtagcc aggaggtgtt ctcatttgtt tttaaaaatg   360
aaaacgtcca actaaatgga aaggacatcg gttggaatag ttacagaaag gagctacaag   420
atgacgagct gaagtctcta caacgagggg cggagaccac ttgggaccaa gcgaggaca    480 tggaatggga gagcgcagtg gatgacatga ccaaaaagca agtatttatt tttgattctt   540
tggttaagaa gtgtttgttt gaagtgctca gcacaaagaa catagctcct agtaatgtta   600
cttggttcgt gcagcatgaa tggggaaagg acccaggctg gcactgtcat gtgctgattg   660
```

```
gaggcaagga ctttagtcaa cctcaaggaa aatggtggag aaggcagcta aatgtgtact      720
ggagtagatg gttggtgact gcctgtaatg ttcaactaac accagctgaa agaattaaac      780
tgagagaaat agcagaggac agtgaatggg tcactttgct tacctataag cataagcaca      840
ccaagaagga ctataccaag tgtgttcttt ttggaaacat gattgcttat tacttttaa       900
gcaaaaagaa aatatgtacc agtccaccaa gggacggagg ctattttctt agcagtgact      960
ctggctggaa aactaacttt ttgaaagagg gcgagcgcca tctagtgagc aaactgtata     1020
ctgatgagat gaaaccagaa acggtcgaga ccacagtgac cactgcacag aagctaagc      1080
gcggcagaat tcaaactaga gaggaggtct cgattaaaac cacactcaaa gagttggtac     1140
ataaaagagt aacctcacca gaagactgga tgatgatgca gccagacagt tacattgaaa     1200
tgatggctca accaggtgga gaaaacttgc ttaaaaatac actagagatc tgtacactga     1260
ctctagcaag aaccaaaaca gcctttgact tgattctgga aaaagctgaa accagcaaac     1320
tagccaactt ttccatggct agcaccagaa cctgtagaat ctttgctgag catggctgga     1380
actatattaa agtctgccat gccatctgtt gtgtgctgaa tagacaagga ggcaaaagga     1440
acactgtgct cttttcacgga ccagccagca caggcaaatc tattattgca caagccatag    1500
cacaagcagt tggtaatgtt ggttgttaca atgctgccaa tgtgaacttt ccatttaatg     1560
actgtaccaa caaaaacttg atttgggtgg aagaagctgg taactttggc cagcaagtaa     1620
accaattcaa agctatttgt tctggccaaa ccatacgcat tgatcaaaaa ggaaaaggca     1680
gcaaacagat tgaaccaaca ccagttatta tgaccaccaa cgagaacatt accgtggtta     1740
gaataggctg tgaggaaaga ccagaacaca ctcaaccaat cagagacaga atgctcaaca     1800
ttcacctgac acgtacacta cctggtgact ttggtttggt ggataagcac gaatggcctc     1860
tgatctgtgc ttggttggtg aagaatggtt accaatctac catggcttgt tactgtgcta     1920
aatggggcaa agttcctgat tggtcagagg actgggcgga gccgaagcta gacactccta     1980
taaattcgct aggttcaatg cgctcaccat ctctgactcc gagaagtacg cctctcagcc     2040
aaaactacgc tcttactcca cttgcatcgg accttgcgga cctagctcta gagccttgga     2100
gcacaccaaa tactcctgtt gcgggcactg cagcaagcca aaacactggg gaggctggtt     2160
ccacagcctg ccaaggtgct caacggagcc caacctggtc cgagatcgag gcggatttga     2220
gagcttgctt cagtcaagaa cagttggaga gcgacttcaa cgaggagctg accttggact     2280
aaggtacaat ggcacctcca gctaaaagag ctaaagagg taagggcta agggatggtt        2340
ggttggtggg gtactaatgt atgactacct gttttacagg cctgaaatca cttggttcta     2400
ggttgggtgc ctcctggcta caagtacctg ggaccaggga acagccttga ccaaggagaa     2460
ccaaccaacc cttctgacgc cgctgccaaa gaacacgacg aagcctacga ccaatacatc     2520
aaatctggaa aaaatcctta cctgtacttc tctcctgctg atcaacgctt cattgaccaa     2580
accaagacg ccaaggactg gggcggcaag gttggtcact acttttttag aaccaagcga     2640
gcttttgcac ctaagctttc tactgactct gaacctggca cttctggtgt gagcagacct     2700
ggtaaacgaa ctaaaccacc tgctcacatt tttgtaaatc aagccagagc taaaaaaaaa     2760
cgcgcttctc ttgctgcaca gcagaggact ctgacaatga gtgatggcac cgaaacaaac     2820
caaccagaca ctggaatcgc taatgctaga gttgagcgat cagctgacgg aggtggaagc     2880
tctgggggtg ggggctctgg cggggtgggg attggtgttt ctactgggac ttatgataat     2940
caaacgactt ataagttttt gggagatgga tgggtagaaa taactgcaca tgcttctaga     3000
cttttgcact tgggaatgcc tccttcagaa aactactgcc gcgtcaccgt tcacaataat     3060
```

```
caaacaacag gacacggaac taaggtaaag ggaaacatgg cctatgacac acatcaacaa    3120
atttggacac catggagctt ggtagatgct aatgcttggg gagtttggtt ccaaccaagt    3180
gactggcagt tcattcaaaa cagcatggaa tcgctgaatc ttgactcatt gagccaagaa    3240
ctatttaatg tagtagtcaa aacagtcact gaacaacaag gagctggcca agatgccatt    3300
aaagtctata ataatgactt gacggcctgt atgatggttg tctctggatag taacaacata    3360 ctgccttaca cacctgcagc tcaaacatca gaaacacttg gtttctaccc atggaaacca    3420
accgcaccag ctccttacag atactacttt ttcatgccta gacaactcag tgtaacctct    3480
agcaactctg ctgaaggaac tcaaatcaca gacaccattg gagagccaca ggcactaaac    3540
tctcaatttt ttactattga gaacaccttg cctattactc tcctgcgcac aggtgatgag    3600
tttacaactg gcacctacat ctttaacact gacccactta aacttactca cacatggcaa    3660
accaacagac acttggcatg cctccaagga ataactgacc taccaacatc agatacagca    3720
acagcatcac taactgcaaa tggagacaga tttggatcaa cacaaacaca gaatgtgaac    3780
tatgtcacag aggctttgcg caccaggcct gctcagattg gcttcatgca acctcatgac    3840
aactttgaag caaacagagg tggcccattt aaggttccag tggtaccgct agacataaca    3900
gctggcgagg accatgatgc aaacggagcc atacgattta actatggcaa caacatggc    3960 gaagattggg ccaaacaagg agcagcacca gaaaggtaca catgggatgc aattgatagt    4020
gcagctggga gggacacagc tagatgcttt gtacaaagtg caccaatatc tattccacca    4080
aaccaaaacc agatcttgca gcgagaagac gccatagctg gcagaactaa catgcattat    4140
actaatgttt taacagcta tggtccactt agtgcatttc ctcatccaga tcccattat    4200 ccaaatggac aaattttggga caaagaattg gacctggaac acaaacctag actacacgta    4260
actgcaccat ttgtttgtaa aaacaaccca ccaggtcaac tatttgttca cttggggcct    4320
aatctgactg accaatttga cccaaacagc acaactgttt ctcgcattgt tacatatagc    4380 acttttttact ggaagggtat tttgaaattc aaagccaaac taagaccaaa tctgacctgg    4440
aatcctgtat accaagcaac cacagactct gttgccaatt cttacatgaa tgttaagaaa    4500
tggctcccat ctgcaactgg caacatgcac tctgatccat tgatttgtag acctgtgcct    4560
cacatgacat actaaccaac caactatgtt tctctgtttg cttcacataa tacttaaact    4620
aactagacta caacataaaa atatacactt aataatagat tattaaaaat aacataatat    4680
ggtaggttaa ctgtaaaaaa taatagaact tttggaataa atatagttag ttggttaatg    4740
ttagatagaa tataaaaga ttttgtattt taaaataaat atagttagtt ggttaatgtt    4800
agatagaata taaaaagatt ttgtatttgg gaaataaaaa gggtggttgg gtggttggtt    4860
ggtactccct tagactgaat gttagggacc aaaaaaataa taaaataatt aaaatgaaca    4920
aggactactg tctattcagt tgaccaactg aacctatagt atcactatgt ttttagggtg    4980 gggggggtggg agatacatac gttcgctatg gaccaagtgg taccggttgg ttgctaagct    5040
cgaacaagac ggctaagccg gtccggttgg ttgagcgcaa ccaaccggta ccacttggtc    5100
catagcgaac gtatgtatct cccaccccccc caccctaaaa acatagtgat actataggtt    5160
cagttggtca actgaa                                                  5176
```